United States Patent
Salibeni et al.

Patent Number: 6,111,114
Date of Patent: Aug. 29, 2000

[54] PROCESS FOR THE PREPARATION OF 4-BROMOMETHYL DIPHENYL COMPOUNDS

[75] Inventors: Aldo Salibeni; Renato Canevotti, both of Milan, Italy

[73] Assignee: Istituto Luso Farmaco D'Italia S.p.A., Milan, Italy

[21] Appl. No.: 09/402,667

[22] PCT Filed: Apr. 6, 1998

[86] PCT No.: PCT/EP98/01992
§ 371 Date: Oct. 19, 1999
§ 102(e) Date: Oct. 19, 1999

[87] PCT Pub. No.: WO98/46562
PCT Pub. Date: Oct. 22, 1998

[30] Foreign Application Priority Data

Apr. 11, 1997 [IT] Italy .............................. MI97A000846

[51] Int. Cl.[7] ...................... C07D 257/04; C07C 255/00; C07C 69/52; C07C 233/00
[52] U.S. Cl. ........................ 548/250; 558/425; 560/205; 564/161
[58] Field of Search ............................ 548/250; 558/425; 560/205; 564/161

[56] References Cited

FOREIGN PATENT DOCUMENTS 0 553 879   8/1993   European Pat. Off. .
0 595 150   5/1994   European Pat. Off. .

OTHER PUBLICATIONS

Patent abstracts of Japan, vol. 014, No. 531, Nov. 21, 1990 and JP 02–221233, Sanko Kagaku Kogyo KK, Sep. 4, 1990.

*Primary Examiner*—Joseph McKane
*Assistant Examiner*—Joseph Murray
*Attorney, Agent, or Firm*—Birch, Stewart, Kolasch & Birch, LLP

[57] ABSTRACT

The compounds of the formula (I) wherein R is as defined in the disclosure, are prepared by bromination of compounds of the formula (II) by means of $Br_2$ or HBr in the presence of $H_2O_2$.

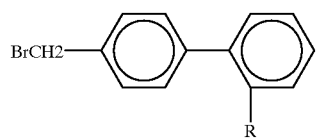

(I)

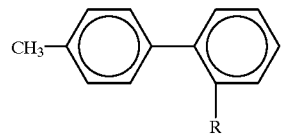

(II)

5 Claims, No Drawings

PROCESS FOR THE PREPARATION OF 4-BROMOMETHYL DIPHENYL COMPOUNDS

The present invention relates to a novel process for the preparation of compounds of general formula I:

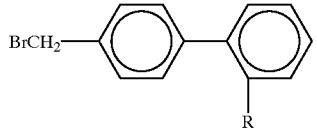

in which R represents CN, $COOR_1$, $CONR_2R_3$ (wherein $R_1$, $R_2$ and $R_3$, which are the same or different, are H, straight or branched $C_1$–$C_6$ alkyl, or $C_3$–$C_6$ cycloalkyl) or optionally substituted tetrazolyl.

Said process provides advantageously on an industrial scale compounds which are key intermediates to the synthesis of biologically active substances, in particular in the field of Angiotensin II antagonists.

Various methods for the synthesis of bromomethyl diphenyl derivatives are known in patent literature. Patents EP 253310, EP 291969 and RP 449699 disclose brominations carried out with N-bromosuccinimide in carbon tetrachloride, in the presence of benzoyl peroxide as a radical initiator, but this method involves safety problems as the solvent used is highly toxic, the radical initiator is explosive and the reactions are very rapid and exothermic thus making the control of the developed heat difficult. Patents EP 553879, JP 6298683 and JP 6298684 disclose bromination methods by means of brominating agents such as bromosuccinimide, bromophthalimide or dibromodimethyl hydantoin in halo or ester solvents in the presence of either initiators such as azobisisobutyronitrile and analogues or of light radiation. These methods solve the safety problem, however they make use of brominating agents much more expensive than those of the present invention and involve the use of thermal initiators which affect costs, or of photochemical initiators poorly suitable to the industrial use. Furthermore, the yields obtained with these procedures are generally lower than those obtainable with the procedure described in the present invention.

On the basis of what described above and as a result of the increasing commercial interest in substituted bromomethyl diphenyl derivatives, as intermediates in the preparation of biologically active compounds, an industrial method for the preparation of these compounds in mild, safe and economically more advantageous conditions is highly interesting.

The process of the present invention relates to the preparation of 4-bromomethyl diphenyl derivatives of general formula I by means of radicalic bromination using bromine or HBr aqueous solutions in the presence of $H_2O_2$, in optionally halo aliphatic or aromatic hydrocarbon solvents of 4-methyl diphenyl compounds of general formula II:

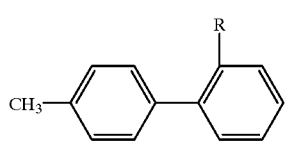

in which R is CN, $COOR_1$, in which $R_1$ is hydrogen or a $C_1$–$C_6$ straight, branched or cyclic alkyl group, $CONR_2R_3$, in which $R_2$ and $R_3$ can be independently hydrogen or a $C_1$–$C_6$ straight, branched or cyclic alkyl group; a tetrazole group, optionally substituted with a tert-butyl, triphenylmethyl group, or another protective group compatible with the reaction conditions, selected for example from those cited in T. Greene P. WUTS "Protective groups in organic chemistry" John Wiley & Sons INC: (1991).

The reaction is carried out using $Br_2$ as brominating agent, in molar ratios ranging between 0.5 and 1 per mol of the diphenyl derivative, or aqueous HBr in concentrations ranging between 48% and 10%, in molar ratios from 1 to 1.5 and in the presence of $H_2O_2$ aqueous solutions in concentrations ranging between 1% and 30%, in molar ratios equivalent to those of the brominating agents.

The solvent used for the reaction consists of a mixture of $H_2O$ and one or more water-immiscible solvents, selected from hydrocarbons, such as hexane, heptane, cyclohexane; halo solvents such as methylene chloride, dibromoethane, bromochloromethane, 1,1,1-trichloroethane; aromatic solvents such as chlorobenzene, t-butylbenzene and the like. The $H_2O$ to solvents ratio is usually 1:1. The reaction temperature can range from 10° C. to the boiling temperature of the organic solvent used, and generally does not exceed 80° C. The reaction times can range from 1 to 25 hours, depending on the substrate, the solvent and the selected temperature.

The process of the invention allows to prepare the compounds of formula I under mild, safe conditions, which are easily applicable on an industrial scale; yields are usually higher than those obtained according to the bromination methods described above, furthermore said process is economically advantageous.

The following examples illustrate the invention without limiting it.

M.p. are not corrected; the identity of the substances and their purity have been established by elementary analysis (CHN) and IR, UV, NMR and mass spectroscopies.

EXAMPLE 1

50 g of 4'-methyl-[1,1'-diphenyl]-2-carbonitrile, 0.5 l of $CH_2Cl_2$, 0.5 l of $H_2O$, 39 ml of 9N aqueous hydrobromic acid and 37 ml of 30% $H_2O_2$ are placed into a three-necked flask fitted with stirrer and condenser. The resulting mixture is stirred at 40° C. for 6 h, then cooled to room temperature. The organic phase is separated and washed twice with 300 ml of $H_2O$, then the solvent is evaporated off until a solid precipitates. The mixture is cooled at 5° C. and stirred at room temperature for 1 h, then filtered, washed with hexane and dried to obtain 60 g of 4'-(bromomethyl)-[1,1'-diphenyl]-2-carbonitrile as a white crystalline solid. Yield: 86% M.P. 120–122° C.

EXAMPLE 2

50 g of 4'-methyl-[1,1'-diphenyl]-2-carbonitrile, 0.5 l of $H_2O$ and 0.5 l of $CH_2Cl_2$ are placed into a three-necked flask fitted with stirrer and condenser, stirring and adding slowly 29 g of $Br_2$ and ml 37 of 30% $H_2O_2$. The reaction mixture is heated to 40° C. and stirred at this temperature for 10 h. Following the procedure described in example 1, 62 g of 4'-(bromomethyl)-[1,1'-diphenyl]-2-carbonitrile as a white crystalline solid are obtained. Yield: 88%.

EXAMPLE 3

Using dichloroethane as solvent and following the procedure described in example 1, the reaction is carried out with stirring at a temperature of 70° C. for 34 h. Following the procedure described in example 1, 55 g of 4'-

(bromomethyl)-[1,1'-diphenyl]-2-carbonitrile as a white crystalline solid are obtained. Yield: 78%.

EXAMPLE 4

10 g of N-tert-butyl-5-(4'-methyl-[1,1'-diphenyl]-2-yl)-1H-tetrazole, 100 ml of $CH_2Cl_2$, 100 ml of $H_2O$, 5.1 ml of 30% $H_2O_2$ and 5.5 ml of 9N aqueous hydrobromic acid are placed into a three-necked flask fitted with stirrer and condenser. The resulting mixture is stirred a 38° C. for 7 h, then cooled, the phases are separated and the organic phase is washed twice with 100 ml of $H_2O$. The solvent is evaporated nearly completely, then 50 ml of hexane are added, stirring for 30' minutes. The precipitate is filtered, washed with hexane and dried. 11.5 g of 5-[(4'-(bromomethyl)-[1,1'-diphenyl]-2-yl]-N-tert-butyl-1H-tetrazole as a white crystalline solid are obtained. Yield: 91%. M.p. 116–118° C.

EXAMPLE 5

10 g of N-tert-butyl-5-(4'-methyl-[1,1'-diphenyl]-2-yl)-1H-tetrazole, 100 ml of $CH_2Cl_2$, 100 ml of $H_2O$, 8.6 ml of $H_2O_2$ 7%, 4 g of $Br_2$ are placed, in this order, into a three-necked flask fitted with stirrer and condenser. The resulting mixture is heated to 38° C. and stirred at this temperature for 8 h. After cooling at room temperature, the procedure described in example 4 is followed. 11 g of 5-[4'-(bromomethyl)[1,1'-diphenyl]-2-yl]-N-tert-butyl-1H-tetrazole as a white crystalline solid are obtained. Yield: 88%.

Comparative Example 1

Following the procedure described in EP 253310, 10 g of 4'-methyl-[1,1'-diphenyl]-2-carbonitrile, 9.2 g of N-bromosuccinimide and 0.2 g of benzoyl peroxide are reacted. The reaction is carried out in carbon tetrachloride under reflux for 3 h. After working up, 8.6 g of 4'-(bromomethyl)-[1,1'-diphenyl]-2-carbonitrile as a white crystalline solid are obtained. Yield: 62%.

Comparative Example 2

Following the procedure described in EP 553879, 10 g of N-tert-butyl-5-(4'-methyl-[1,1'-diphenyl]-2-yl)tetrazole, 6.1 g of N-bromosuccinimide and 8.7 mg of 2,2'-azobis-2,4-dimethylvaleronitrile are reacted. The reaction is carried out in methylene chloride at an inner temperature of 42° C. for 20 h. After working up, 9.5 g of N-tert-butyl-5-[4'-(bromomethyl)-[1,1'-diphenyl]-2-yl]-tetrazole as a crystalline white solid are obtained. Yield: 75%.

What is claimed is:

1. A process for the preparation of 4-bromomethyl diphenyl derivatives of general formula I

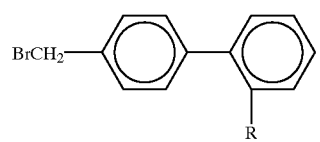

I in which R represents CN, $COOR_1$, $CONR_2R_3$ (wherein $R_1$, $R_2$ and $R_3$, which are the same or different, are H, straight or branched $C_1$–$C_6$ alkyl, or $C_3$–$C_6$ cycloalkyl, or optionally substituted tetrazolyl, which process comprises brominating compounds of general formula II

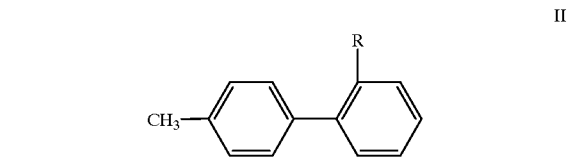

II in which R has the same meanings as in formula I, using $Br_2$ or HBr aqueous solutions, in the presence of $H_2O_2$ aqueous solutions and of optionally halo aliphatic or aromatic hydrocarbon solvents, at temperatures ranging between 10° C. and the boiling temperature of the solvents used.

2. A process according to claim 1, in which R is a CN group or a tetrazol-5-yl group having a tert-butyl group at the 1- or 2- position.

3. A process according to claim 1, in which R is a tetrazol-5-yl group having a triphenylmethyl group at the 1- or 2- position.

4. A process according to claim 1, in which the solvent is a mixture of $H_2O$ and of one or more solvents selected from the group consisting of: hexane, heptane, methylene chloride, bromochloromethane, dibromoethane, chlorobenzene, tert-butylbenzene, dichloroethane.

5. A process according to claim 1, in which the brominating agent is $Br_2$ or HBr aqueous solutions in the presence of $H_2O_2$ aqueous solutions.

* * * * *